United States Patent [19]

Schumann

[11] Patent Number: Plant 7,422

[45] Date of Patent: Jan. 15, 1991

[54] GERANIUM PLANT NAMED FISRIX

[75] Inventor: Ingeborg Schumann, Hoehr-Grenzhausen, Fed. Rep. of Germany

[73] Assignee: Florfis AG, Binningen, Switzerland

[21] Appl. No.: 426,223

[22] Filed: Oct. 25, 1989

[51] Int. Cl.[5] ..... A01H 5/00

[52] U.S. Cl. ..... Plt./68

[58] Field of Search ..... Plt./68

[56] References Cited

U.S. PATENT DOCUMENTS

P.P. 6,636 2/1989 Winner ..... Plt. 68

*Primary Examiner*—James R. Feyrer

*Attorney, Agent, or Firm*—Foley & Lardner, Schwawrtz, Jeffery, Schwaab, Mack, Blumenthal & Evans

[57] ABSTRACT

A new and distinct cultivar of Geranium plant named Fisrix, particularly characterized by the combined features of single flowers having a purplish pink main color and unique markings of much redder color near the center of each petal, dark foliage, early flowering, fast rooting, very good heat tolerance and very little shattering.

1 Drawing Sheet

The present invention comprises a new and distinct cultivar of Geramium, botanically known as *Pelargonium zonale,* and hereinafter referred to by the cultivar name Fisrix.

Fixrix is a product of a planned breeding program which had the objective of creating new Geranium cultivars with dark green leaves, new color and flower type, fast rooting, good branching and early flowering.

Fisrix was originated from a hybridization made by the inventor in a controlled breeding program in Hillscheid, Federal Republic of Germany, in 1982. The female parent was an inbred line identified as No. 94, characterized by its pink color with dark eye in the flower, single flower form, rich flowering and very fast rooting. The male parent of Fisrix was a tetraploid line of the cultivar Stadt Bern, characterized by its dark green leaves, small single flowers, and its slow growth in winter.

Fisrix was discovered and selected as one flowering plant within the progeny of the stated cross by Ingeborg Schumann in May 1983 in a controlled environment in Hillscheid, Federal Republic of Germany.

The first act of asexual reproduction of Fisrix was accomplished when vegetative cuttings were taken from the initial selection in February 1984 in a controlled environment in Hillscheid, Federal Republic of Germany by, or under the supervision, of Ingebord Schumann.

Horticultural examination of selected units initiated in Spring 1984 and continuing thereafter has demonstrated that the combination of characteristics as herein disclosed for Fisrix are firmly fixed and are retained through successive generations of asexual reproduction.

Fisrix has not been observed under all possible environmental conditions. The phenotype may vary significantly with variations in environment such as temperature, light intensity and daylength.

The following observations, measurements and comparisons describe plants grown in Hillscheid, Federal Republic of Germany, under greenhouse conditions which approximate those generally used in commercial practice.

The following traits have been repreatedly observed and are determined to be basic characteristics of Fisrix, which, in combination, distinguish this Geranium as a new and distinct cultivar:

1. Completely new type flower form for pelargoniums, appearing similar in many respects to phlox.
2. Single pink flowers with a dark center. The center is formed by blotches or marks on each petal near the center, with the marks not extending the width of its petal in that area. A unique, discontinuous area much darker in color than the main petal color provides a spoke-like effect at the flower center, an entirely new coloration.
3. Dark green leaves.
4. Zonation very little to weak.
5. Early flowering.
6. Fast rooting.
7. Superb chlorophyll quality for better transportation.
8. Nearly no shattering of the flower petals.

Of the many pelargonium cultivars known to the present inventor, there is none to which a meaningful comparison can be made. The combined characteristics as described define a unique new pelargonium.

The accompanying color photographic drawing shows typical flower and foliage characteristics of Fisrix, with the colors being as true as possible with illustrations of this type.

In the following description color references are made to The Royal Horticultural Society Color Chart and in certain instances to the Horticultural Color Chart (HCC). The color values were determined between 10:00 a.m. and 11:00 a.m. on May 9, 1987 under 55,000 Lux light intensity indoors at Hillscheid, Federal Republic of Germany.

Classification:

*Botanical.*—A hybrid of the genua *Pelargonium zonale* l'hert. cv Fisrix.

*Commercial.*—Zonal geranium.

INFLORESCENCE

A. Umbel:

*Average diameter.*—Indoor, 10.0 cm; outdoor, 11.6 cm.

*Average depth.*—Indoor, 5.2 cm; outdoor, 5.9 cm.

*Peduncle length.*—Indoor, 13.0 cm; outdoor, 13.9 cm.

*Pedicel length.*—Indoor, 3.9 cm; outdoor, 3.5 cm.

B. Corolla:

*Average diameter.*—Indoor, 4.0 cm; outdoor, 4.1 cm.

*Form.*—Single.

*Color (general tonality from a distance of three meters).*—Purplish pink, 68C.

*Color (upper surface).*—RHS 68B; HCC 627/1.

*Color (near center).*—RHS 57A; HCC 724.

*Sepals.*—Red with green tip.

*Pedicels.*—Red.

C. Bud:

*Shape.*—Narrow elliptic.

*Color.*—Red, upper half green.

*Sepals.*—Dark green, turn red when flower opens.

*Pedicels.*—Red, some with spur.

D. Reproductive organs:

*Androecium.*—6–7 stamens.

*Gynoecium.*—5 lobed stigma.

E. Spring flowering response period: In Hillscheid, Federal Republic of Germany in 1988, 66% of plants with at least 1 flower opened 12 weeks after planting of unrooted cuttings in week 5.

F. Outdoor flower production: The flower count in 1988 in Hillscheid, Federal Republic of Germany indicated between 53 and 58 flowers per plant for June through October observation period.

G. Durability: Excellent rain resistance; nearly no shattering.

PLANT

A. Foliage:

*Form.*—Kidney shaped.

*Margin.*—Bicrenate.

*Color.*—Dark green.

*Zonation.*—Very weak.

*Tolerance to botrytis.*—Good.

B. General appearance and form:

*Internode length.*—Medium to short.

*Branching pattern.*—2.5 branches per plant after 13 weeks of growing time from unrooted cuttings.

*Height.*—24 cm on average.

I claim:

1. A new and distinct cultivar of Geranium plant named Fisrix, as illustrated and described.

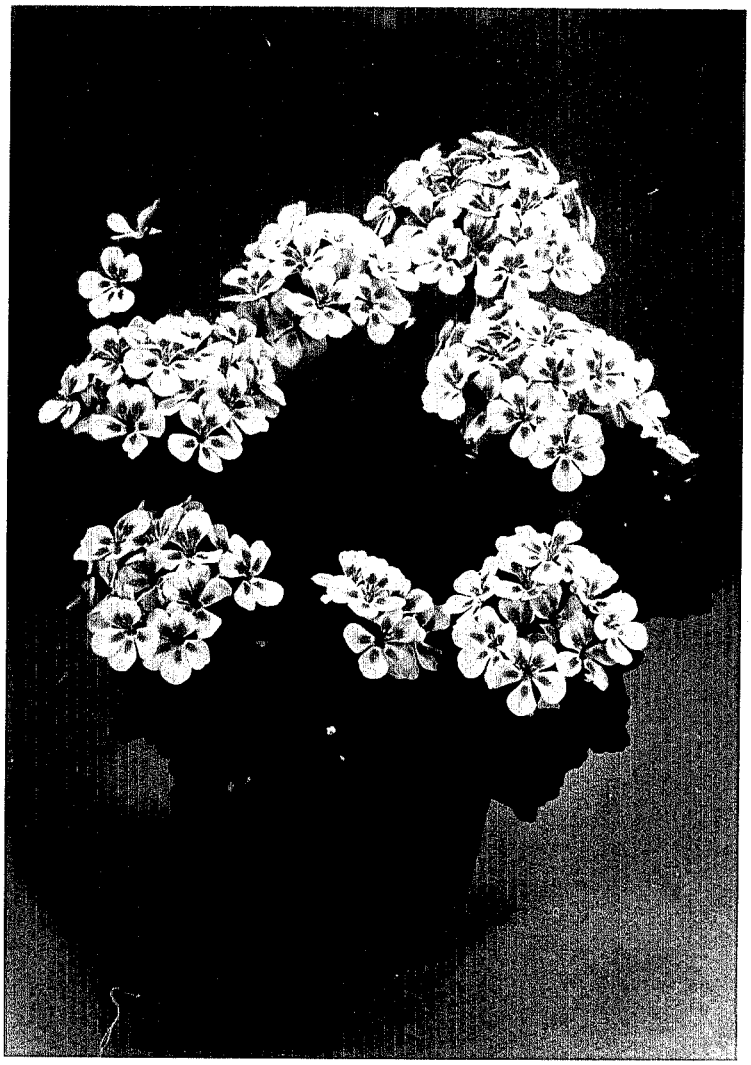

* * * * *